United States Patent [19]

Weitz et al.

[11] Patent Number: 4,506,096
[45] Date of Patent: Mar. 19, 1985

[54] 2-ALKYL-2,4-DIACYLOXY-BUT-3-ENALS

[75] Inventors: Hans-Martin Weitz, Bad Durkheim; Rolf Fischer, Heidelberg; Joachim Paust, Neuhofen, all of Fed. Rep. of Germany

[73] Assignee: BASF Aktiengesellschaft, Ludwigshafen, Fed. Rep. of Germany

[21] Appl. No.: 473,773

[22] Filed: Mar. 10, 1983

[30] Foreign Application Priority Data

Mar. 24, 1982 [DE] Fed. Rep. of Germany ....... 3210707

[51] Int. Cl.³ .................... C07C 69/007; C07C 69/16; C07C 69/28; C07C 69/78
[52] U.S. Cl. ................................. 560/262; 260/405.6; 260/406; 260/410.6; 560/1; 560/112; 560/122; 568/447; 585/351
[58] Field of Search ................... 560/262, 1, 122, 112; 260/410.6, 405.6, 406

[56] References Cited

U.S. PATENT DOCUMENTS 3,639,437  2/1972  Fischer et al. .................... 560/262
4,124,619  11/1978  Fitton et al. ....................... 560/262
4,284,796  8/1981  Fischer et al. .................... 560/262

Primary Examiner—Vivian Garner
Attorney, Agent, or Firm—John H. Shurtleff

[57] ABSTRACT

2-Alkyl-2,4-diacyloxy-but-3-enals of the formula

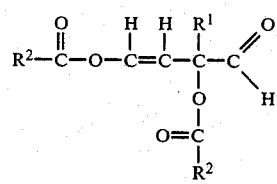

where $R^1$ is alkyl and $R^2$ is hydrogen, alkyl, a cycloaliphatic radical or an aromatic radical, are prepared by reacting a buta-1,3-diene of the formula

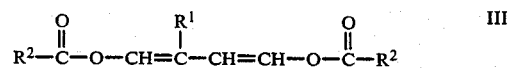

with an oxygen donor. The new compounds are valuable intermediates in the preparation of terpenes, e.g. retinal, β-carotin and apocarotinoids.

3 Claims, No Drawings

2-ALKYL-2,4-DIACYLOXY-BUT-3-ENALS

The present invention relates to novel 2-alkyl-2,4-diacyloxy-but-3-enals and to a process for their preparation by reacting 2-alkyl-1,4-diacyloxy-buta-1,3-dienes with oxygen donors.

European Patent 5,452 discloses that the reaction of 1-acyloxy-2-alkyl-buta-1,3-dienes with carboxylic acids and oxygen in the presence of palladium-containing or platinum-containing catalysts gives 2-alkyl-1,1,4-triacyloxy-but-2-enes.

We have found novel 2-alkyl-2,4-diacyloxy-but-3-enals of the formula

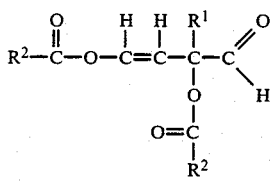

where $R^1$ is alkyl of 1 to 5 carbon atoms and $R^2$ is hydrogen, alkyl of 1 to 15 carbon atoms, a cycloaliphatic radical of 5 to 7 carbon atoms or an aromatic radical.

Examples of alkyl of 1 to 5, or 1 to 15, carbon atoms are methyl, ethyl, n-propyl, i-propyl, n-butyl, i-butyl, tert.-butyl, n-pentyl, palmityl and stearyl. Examples of suitable cycloaliphatic radicals are cylcopentyl, cyclohexyl and cycloheptyl. Examples of aromatic radicals are phenyl which is unsubstituted or substituted by alkyl or halogen, e.g., phenyl, 2-chlorophenyl, 2,4-dichlorophenyl, 2-methylphenyl, and 2,4-dimethylphenyl.

2-Alkyl-2,4-diacyloxy-but-3-enals of the formula

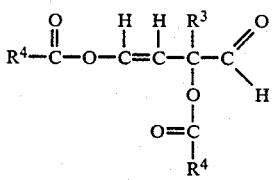

where $R^3$ is alkyl of 1 to 3 carbon atoms and $R^4$ is hydrogen or alkyl of 1 to 3 carbon atoms are of particular industrial interest. 2-Methyl-2,4-diacetoxy-but-3-enal is especially preferred.

The invention further relates to a process for the preparation of the 2-alkyl-2,4-diacyloxy-but-3-enals of the formula I, wherein a buta-1,3-diene of the formula

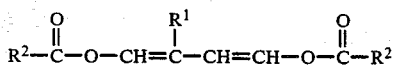

where $R^1$ and $R^2$ have the above meanings is treated with an oxygen donor in a solvent which is inert under the reaction conditions.

In the case of the reaction of 2-methyl-1,4-diacetoxy-buta-1,3-diene with m-chloroperbenzoic acid in chloroform, to give 2-methyl-2,4-diacetoxy-but-3-enal, the reaction can be represented by the following formulae:

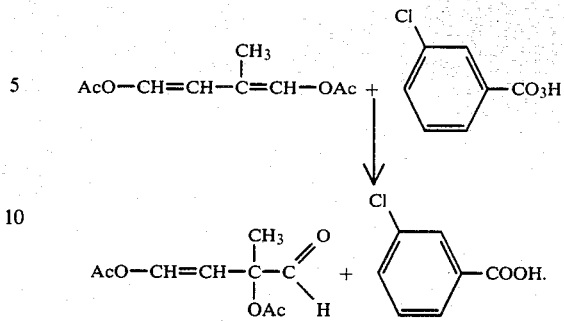

Examples of 2-alkyl-1,4-diacyloxy-buta-1,3-dienes of the formula III are 2-methyl-, 2-ethyl-, 2-n-propyl-, 2-butyl-, 2-pentyl-1,4-diacetoxy-buta-1,3-diene, 2-methyl-1-acetoxy-4-palmityloxy-buta-1,3-diene, 2-methyl-1-cyclohexyloxy-4-acetoxy-buta-1,3-diene and 2-methyl-1-benzoyloxy-4-acetoxy-buta-1,3-diene.

Starting materials of the formula III may be prepared, for example, by acetylating a 2-alkyl-4-acyloxy-but-2-enal with acetic anhydride (J. org. Chem. 41, [1976], 2625) or by pyrolyzing a 2-alkyl-3,4-diacetoxy-tricyclo[4.2.1.0$^{2.5}$]-non-7-ene (J. Chem. Soc., Chem. Comm., 1974, 956).

Examples of suitable oxygen donors are aromatic percarboxylic acids, e.g., perbenzoic acid and m-chloroperbenzoic acid, and organic hydroperoxides, e.g., tert.-butyl hydroperoxide and cumene hydroperoxide. Compounds of this type are to be found, for example, in Ullmanns Encyclopädie der Technischen Chemie, 4th Edition, Volume 10, pages 563–567. The oxygen donor can also be used in the presence of a catalyst, for example a catalyst containing a metal such as boron, tin, arsenic, titanium, zirconium, vanadium, molybdenum or tungsten, or which consists of compounds of these metals. The amount of oxygen donor used per mole of 1,3-diene of the formula III is, for example, from 0.5 to 10 moles, especially from 1 to 1.5 moles.

The reaction is carried out in the presence of a solvent which is inert under the reaction conditions. Examples of suitable solvents of this type are carboxylic acid esters, e.g., methyl acetate, chlorohydrocarbons, e.g. methylene chloride, chloroform, carbon tetrachloride or 1,2-dichloroethane, hydrocarbons, e.g., alkanes, benzene and alkylated benzenes, and ethers, e.g., diethylether, tetrahydrofuran and dioxane. Advantageously, from 0.1 to 80 moles, especially from 2 to 60 moles, of the solvent which is inert under the reaction conditions are used per mole of starting compound of the formula III.

The process according to the invention is advantageously carried out at from −20° to 200° C., especially from 20° to 120° C., and can be effected batchwise or continuously, and under atmospheric or superatmospheric pressure. Unconverted 1,3-dienes can, where appropriate, be separated by distillation, after the reaction, from the 2-alkyl-2,4-diacyloxy-but-3-enals formed, and be reused for the reaction according to the invention.

In batchwise operation the reaction may, for example, be carried out as follows: the oxygen donor is added to a solution of the 1,3-diene in the particular solvent at the reaction temperature and under the reaction pressure. After completion of the addition, stirring is continued if appropriate. Where necessary, nitrogen is passed through the reaction mixture when it has cooled to room temperature. Thereafter the solvent is distilled off and the residue is then subjected to fractional distillation. This separates off any unconverted starting compounds from the desired aldehydes.

The novel 2-alkyl-2,4-diacyloxy-but-3-enals of the formula I obtainable by the process according to the invention can be rearranged to 2-alkyl-4,4-diacyloxy-but-2-enals, for example by treatment with aliphatic carboxylic acids in the absence of strong acids, and are therefore valuable intermediates for the preparation of terpenes, e.g., retinal, β-carotin (German Laid-Open Application DOS No. 2,357,810) and apocarotinoids.

EXAMPLE 1,300 g of a chloroform solution containing 86 g of m-chloroperbenzoic acid and 15 g of m-chlorobenzoic acid were added over two hours to a stirred solution of 92 g of 2-methyl-1,4-diacetoxy-buta-1,3-diene in 1,300 g of chloroform at 30±2° C. Stirring was continued for a further hour at the same temperature, after which unconverted peracid was no longer detectable in the reaction mixture. The chloroform phase was washed first with a total of 1,000 cm$^3$ of water containing 84 g of sodium bicarbonate and then with 200 cm$^3$ of water, and was dried over magnesium sulfate. The chloroform was stripped off on a rotary evaporator. Fractional distillation of the residue gave 50.5 g of a mixture of boiling point 80°–96° C./0.5 mbar, $n_D^{20}=1.4598$, which according to the $^1$H-NMR spectrum contained 31 g of 2-methyl-2,4-diacetoxy-but-3-enal (31%, based on diene employed) and 16.8 g of 2-methyl-4,4-diacetoxy-but-2-enal (17%, based on diene employed).

$^1$H-NMR spectra (CDCl$_3$ as solvent, TMS as internal standard):

(E)-2-Methyl-2,4-diacetoxy-but-3-enal: δ=1.55 (s, —CH$_3$, 3H), about 2.15 (s, —CO—CH$_3$, 6H); 5.48 (d, —C—CH=, J=13 Hz, 1H), 7.41 (d, —O—CH=, J=13 Hz, 1H), 9.28 (s, —CHO, 1H).

(Z)-2-Methyl-2,4-diacetoxy-but-3-enal: δ=1.58 (s, —CH$_3$, 3H), about 2.15 (s, —CO—CH$_3$, 6H), 5.15 (d, —C—CH=, J=7 Hz, 1H), 7.10 (d, —O—CH=, J=7 Hz, 1H), 9.37 (s, —CHO, 1H).

We claim:

1. A 2-alkyl-2,4-diacyloxy-but-3-enal of the formula

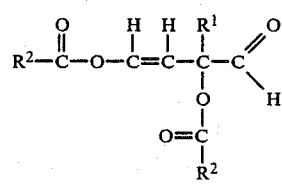

where R$^1$ is alkyl of 1 to 5 carbon atoms and R$^2$ is hydrogen, alkyl of 1 to 15 carbon atoms, a cycloaliphatic radical of 5 to 7 carbon atoms, phenyl or phenyl substituted by alkyl or halogen.

2. A 2-alkyl-2,4-diacyloxy-but-3-enal of the formula

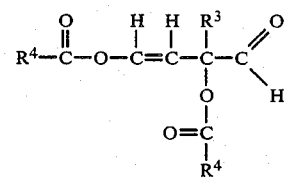

where R$^3$ is alkyl of 1 to 3 carbon atoms and R$^4$ is hydrogen or alkyl of 1 to 3 carbon atoms.

3. 2-Methyl-2,4-diacetoxy-but-3-enal.

* * * * *